United States Patent [19]
DelVillano, Jr. et al.

[11] Patent Number: 5,126,243
[45] Date of Patent: * Jun. 30, 1992

[54] IMMUNOASSAY FOR CARBOHYDRATE ANTIGENIC DETERMINANT

[75] Inventors: Bert C. DelVillano, Jr., Berwyn; Yu-Sheng V. Liu, Malvern, both of Pa.

[73] Assignee: Centocor, Inc., Malvern, Pa.

[ * ] Notice: The portion of the term of this patent subsequent to Nov. 8, 2005 has been disclaimed.

[21] Appl. No.: 268,021

[22] Filed: Nov. 7, 1988

Related U.S. Application Data

[63] Continuation of Ser. No. 919,569, Oct. 20, 1986, Pat. No. 4,783,420, which is a continuation of Ser. No. 600,551, Apr. 6, 1984, abandoned.

[30] Foreign Application Priority Data

Aug. 9, 1982 [US] United States ....... PCT/US82/01078

[51] Int. Cl.$^5$ ........................................... G01N 33/574
[52] U.S. Cl. .................... 435/7.23; 435/962; 436/534; 436/518; 436/813
[58] Field of Search ............ 436/518, 811, 813; 424/88; 435/7, 7.23

[56] References Cited

U.S. PATENT DOCUMENTS 4,086,217 4/1978 Hansen .................. 424/88
4,180,499 12/1979 Hansen .................. 424/88
4,783,420 3/1988 DelVillano, Jr. et al. ......... 436/518

FOREIGN PATENT DOCUMENTS 043359 2/1981 European Pat. Off. .

OTHER PUBLICATIONS

Steplewski, Z., et al., Eur. J. Immunol., vol. 9, pp. 94–96 (Jan. 1979).
Koprowski, H., et al., Somatic Cell Genetics, vol. 5(6), pp. 957–972 (1979).
Magnani, J. L. et al., Science, vol. 212(3), pp. 55–56 (Nov. 1980).
Ishikawa, E., et al., Journal of Immunoassay 1(3), pp. 385–398 (1980).
Brockhaus et al., *Archives of Biochemistry and Biophysics*, 217:647–651 (1981).
Mosmann et al., *The Journal of Immunology*, 125:1152–1156 (1980).
Magnani et al., *The Journal of Biological Chemistry*, 257:14365–14369 (1982).

*Primary Examiner*—Esther L. Kepplinger
*Assistant Examiner*—Donna C. Wortman
*Attorney, Agent, or Firm*—Hamilton, Brook, Smith & Reynolds

[57] ABSTRACT

An immunoassay for a carbohydrate antigenic determinant, such as CA 19-9, is disclosed in which the primary antigen-antibody reaction is carried out under acidic conditions.

4 Claims, 3 Drawing Sheets

IMMUNOASSAY FOR CARBOHYDRATE ANTIGENIC DETERMINANT

RELATED APPLICATION

The instant application is a continuation of U.S. Ser. No. 06/919,569, filed Oct. 20, 1986, issued Nov. 8, 1988, U.S. Pat. No. 4,783,420, which is a continuation of U.S. national application, U.S. Ser. No. 06/600,551, filed Aug. 6, 1984, now abandoned, U.S. designation of PCT Application U.S. 82/01078, filed Aug. 9, 1982.

TECHNICAL FIELD

This invention is in the field of immunology and particularly relates to an immunoassay for detecting a carbohydrate antigenic determinant.

BACKGROUND ART

Monoclonal antibodies are antibodies which have been produced by a cell line cloned from a single antibody producing cell. Monoclonal antibodies are extraordinarily pure, uniform and reproducible since each antibody is effective against a single antigenic determinant.

Monoclonal antibodies can be obtained in significant quantities from hybridoma cells. Hybridoma cells are fused cells resulting from the fusion of antibody producing cells with tumor cells. The initial work relating to the production of such hybridoma cells was done by Cesar Milstein and George Kohler employing mouse myeloma cells with spleen cells taken from mice immunized with sheep red blood cells. See, Kohler et al., *Eur. J. Immunol.*, 6, 511–19 (1976); Kohler et al., *Nature*, 256, 495–7 (1975); and Milstein, *Scientific American*, 243 (4), 66–74 (1980).

More recently, Hilary Koprowski and colleagues have extended the original hybridoma work by developing hybridoma cell lines capable of producing monoclonal antibodies against specific viruses and tumors. See, U.S. Pat. Nos. 4,196,265 and 4,172,124, respectively. Wands and Zurawski further extended hybridoma technology to produce hybridoma cell lines capable of producing monoclonal antibodies to hepatitis virus. See U.S. Pat. No. 4,271,145. It has also been recently discovered that monoclonal IgM antibodies produced from hybridoma cell lines can be employed in certain immunoassays to improve the sensitivity and specificity thereof. See, U.S. application Ser. No. 188,735, filed Sep. 19, 1980, in the names of Jack R. Wands, Vincent R. Zurawski, and Hubert J. P. Schoemaker.

Even more recently, a monoclonal antibody, designated 1116 NS 19-9 (hereinafter "19-9 antibody"), was developed by Koprowski et al. by immunization of BALB/c mice with a human colorectal cancer cell line, SW1116. See Koprowski, H., Steplewski, Z., Mitchell, K., Herlyn, M., Herlyn, D., and Fuhrer, P., Colorectal carcinoma antigens detected by hybridoma antibodies, *Somatic Cell Genetics*, 5, 957–972, (1979). It has been shown that the 19-9 antibody reacts with a carbohydrate antigenic determinant (hereinafter referred to as "CA 19-9") which has been identified as a sialylated lacto-N-fucopentaose II, an oligosaccharide which shares structural features with Lewis blood group substances. See Magnani, J., Nilsson, B., Brockhaus, M., Zopf, D., Steplewski, Z., Koprowski, H., Ginsburg, V., The antigen of a tumor—specific monoclonal antibody is a ganglioside containing sialylated lacto—N-Fucopentaose II, Fed. Proc. 41, 898, (1982).

In early studies using a competition radio-immunoassay, the 19-9 antibody was shown to have high sensitivity in identifying patients with gastrointestinal adenocarcinomas and to have high specificity for normal individuals. See Koprowski, H., Herlyn, H., Steplewski, Z., and Sears, H. F., Specific antigen in serum of patients with colon carcinoma, *Science*, 212, 53, (1981); and, Herlyn, M., Clark, W. H., Mastrangelo, J. J., Guerry, D., Elder, D. E., Larossa, D., Hamilton, R., Bondi, E., Tutkill, R., Steplewski, Z., Koprowski, H., Specific antigens to colorectal carcinoma in sera of patients are detected by monoclonal antibodies, Cancer Res. 40, 3602–3609, (1982). The CA 19-9 epitope has also been identified on a glycolipid extracted from SW1116 cells and from meconium, as well as on a glycoprotein from SW1116 cells. See Magnani, J., Brockhaus, M., Smith, D., Ginsburg, V., Blaszcyk, M., Mitchell, D., Steplewski, Z., and Koprowski, H., A Monoclonal Antibody Defined Antigen of colon Carcinoma, *Science* 212, 55, (1981).

Disclosure of the Invention

This invention relates, in its broadest aspects, to immunoassays for detecting carbohydrate antigenic determinants.

In one embodiment, a forward sandwich immunoassay is employed to detect the CA 19-9 antigen. In this assay, a patient sample containing the antigen is initially incubated with a solid-phase immunoadsorbent containing immobilized 19-9 antibody. Incubation is continued for a sufficient period of time to allow antigen in the patient sample to bind to immobilized antibody on the solid-phase immunoadsorbent. After this first incubation, the solid-phase immunoadsorbent is separated from the incubation mixture and washed to remove excess antigen and other interfering substances, such as non-specific binding proteins, which also may be present in the patient sample. The solid-phase immunoadsorbent containing antigen bound to immobilized antibody is subsequently incubated for a second time with labeled antibody capable of binding to CA 19-9 antigen. After the second incubation, another wash is performed to remove unbound labeled antibody from the solid-phase immunoadsorbent thereby removing non-specifically bound labeled antibody. Labeled antibody bound to the solid-phase immunoadsorbent is then detected and the amount of labeled antibody detected serves as a direct measure of the amount of CA 19-9 antibody present in the original patient sample.

The immunoassay is preferably carried out under conditions whereby the antigen-antibody reaction occurs at acidic pH. This is because it has been surprisingly found that higher signal/noise ratios can be achieved under such conditions.

The resulting assay has high sensitivity for patients with gastrointestinal adenocarcinomas, especially pancreatic cancer, and has very high specificity, even among patients with benign gastrointestinal disease.

BEST MODE FOR CARRYING OUT THE INVENTION

Figure 1:
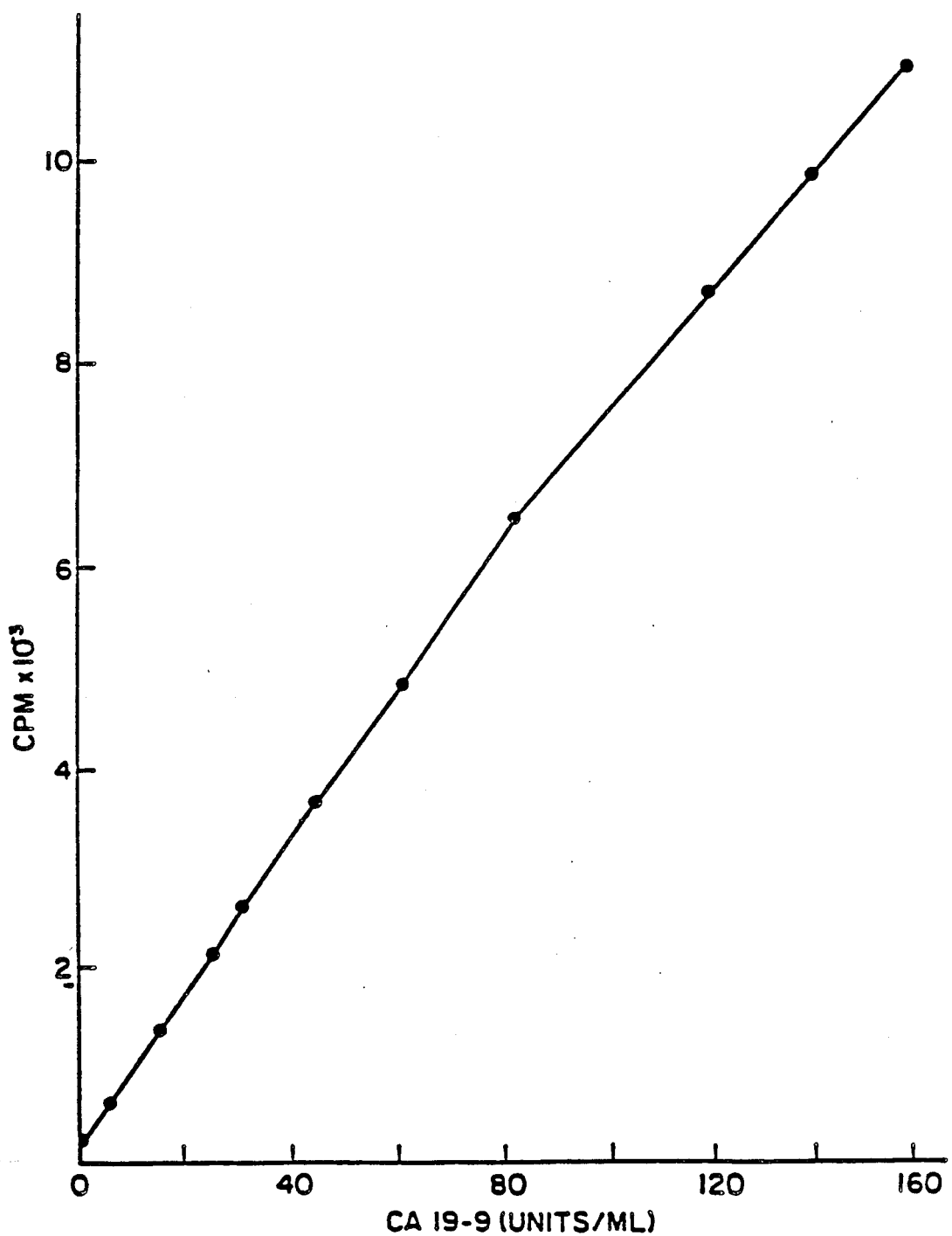
FIG. 1 is a standard curve prepared for CA 19-9, which illustrates the sensitivity of a sandwich immunoassay of CA19-9 antibody coated beads and $^{125}$I labeled CA19-9 antibody for increasing amounts of CA19-9 antigens.

Although most of the experimental work described below was carried out at a pH of 4.5, it should be recognized that other acidic pHs could have been employed. This would especially be true for carbohydrate antigenic determinants other than CA 19-9, or antibodies other than the 19-9 antibody. With regard to detecting CA 19-9 antigen with 19-9 antibody, the preferred pH range was found to be from about 2.5 to about 6.5, and it is especially preferred to operate at a pH of about 4.5.

Similarly, the experimental work described herein relates to a forward sandwich assay. Nevertheless, it is believed that carbohydrate antigenic determinants can be determined in many cases employing acidic conditions with reverse sandwich assays or simultaneous sandwich assays.

In addition to labeling antibody with radioactive labels, other labels, such as fluorescent materials, could also be employed. Further, enzyme labels could be employed, in which case detection could be achieved by a colorimetric method employing a competing substrate for the enzyme label.

The forward sandwich assay for CA 19-9 will now be more specifically illustrated by way of the following example.

EXAMPLE

Murine hybridoma 1116-NS-19-9 was obtained from Dr. Z. Steplewski (Wistar Institute, Philadelphia, Pa.). Hybridoma cells were grown in tissue culture and were used to prepare ascitic fluid in pristane primed BALB/c mice. IgG was purified from ascites by affinity chromatography on protein A-Sepharose (Pharmacia) using elution at pH 4.0. Purity of the isolated IgG was demonstrated by SDS polyacrylamide gel electrophoresis, isoelectric focusing and immunoelectrophoresis.

Purified antibody was radioiodinated using $^{125}$I labeled N-hydroxysuccinimide ester of p-hydroxyliodophenylpropionic acid, Bolton-Hunter reagent, using the manufacturer's recommended procedure. Specific activity of the $^{125}$I IgG ranged from 5 to 15 $\mu$Ci/$\mu$gm. Polystyrene beads ($\frac{1}{4}$"; Precision Plastic Ball Co., Chicago, Ill.) were coated with purified antibody and dried.

Experimental samples were assayed in duplicate using a "forward sandwich" radioimmunometric assay. One hundred microliters of sera, standard solutions or controls were mixed with 100 $\mu$l of buffer (5 mg/ml bovine serum albumin, Armour Pharmaceutical, So. Plainfield, N.J.; 50 mM sodium citrate; 1 mM ethylene diamine tetracetic acid; pH 3.0) in a reaction tray. An antibody coated bead was added and samples were incubated at 37° for 3 hours. Beads were washed with deionized water, then 200 $\mu$l of $^{125}$I labeled 19-9 antibody (130,000 dpm; 5 mg/ml bovine serum albumin; 50 mM sodium citrate; pH 4.5) was added. Samples were then incubated for 3 hours at room temperature (18-22°). Beads were washed and then counted in a gamma counter.

Experimental results were converted into units by comparison with a standard curve prepared as follows. Partially purified CA 19-9 was diluted into pooled reconstituted human serum to give concentrations between 6 and 160 units/ml. One hundred microliters of standards were mixed with 100 $\mu$l of buffer and an 19-9 antibody coated bead for 3 hours at 37°. Beads were washed with dH$_2$O then $^{125}$I labeled 19-9 antibody (130,000 dpm) was added and incubated for 3 hours at 20° C. After washing, $^{125}$I bound to beads was determined using a gamma counter. The resulting standard curve is illustrated as FIG. 1.

Frozen coded samples from the National Cancer Institute (NCI) serum bank were provided by Dr. R. Herberman (NCI). Serum was carefully prepared and frozen continuously at $-70°$. Clinical data were compiled from reports provided by Dr. V. Go (Mayo Clinic). Additional serum samples from random healthy blood bank donors were obtained from Dr. J. Menitove, Southeastern Blood Center of Milwaukee, Wis. All donors qualified as blood donors, and were negative when tested for hepatitis B surface antigen. Data concerning age and sex were provided by Dr. Menitove.

The levels of CA 19-9 were determined by plotting $^{125}$I]-19-9 bound versus the concentration of CA 19-9 in standard solutions. The CA 19-9 concentration of each standard was specified in arbitrary units. As shown in FIG. 1, the amount of $^{125}$I labeled 19-9 antibody bound approximated a linear function of concentration up to at least 80 units/ml. The intra- and interassay coefficients of variation were 5-12% in the range between 5 and 120 units/ml and the minimum detectable dose was 1.5 units/ml.

Figure 2:
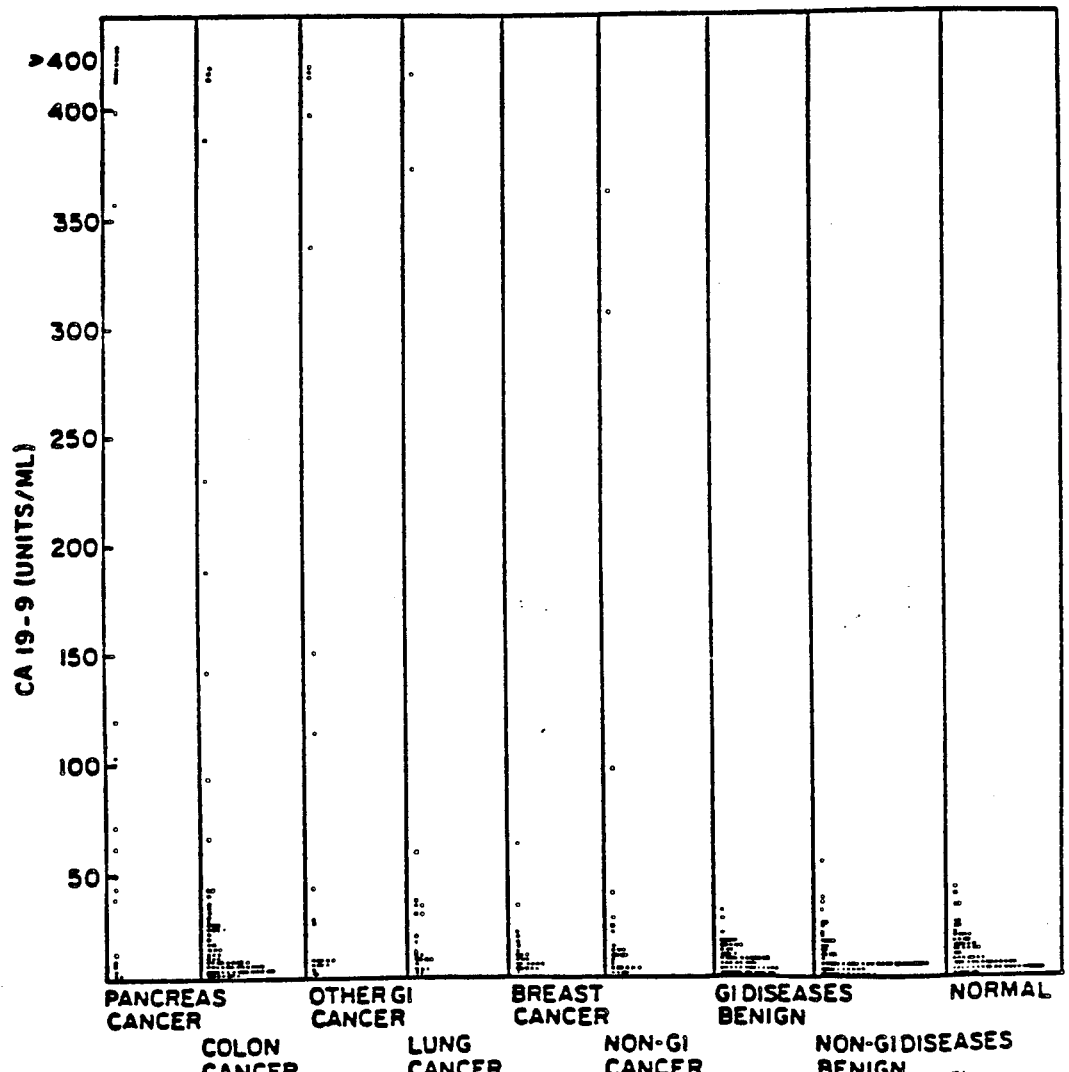
FIG. 2 is a depiction of the CA 19-9 concentration in patient sera for patients having different types of cancer or benign diseases.

The concentration of CA 19-9 in sera from a coded panel from the Mayo Clinic - NCI and in sera from blood bank donors was determined using the CA 19-9 assay. Four hundred and eleven samples from the Mayo Clinic-NCI Serum Bank were assayed. As shown in FIG. 2, the level of CA 19-9 in the serum of cancer patients was frequently higher than that in the serum of normal individuals or of patients with benign diseases. Using an arbitrary value of 37 units/ml to discriminate between positive and negative samples, sera from 19 of 25 (74%) pancreatic cancer patients were found to contain elevated levels of CA 19-9. Among 75 patients with colorectal cancer, 12 (16%) had CA 19-9 levels above 37 units/ml, including 6 of 23 (26%) having distant metastasis, 4 of 25 (16%) Dukes B and C, and 2 of 27 (7%) Dukes A Disease. Elevated levels of CA 19-9 were also observed in 10 of 31 (32%) sera of patients with other gastrointestinal malignancies (Table 1). High concentrations were usually associated with adenocarcinomas of the hepatobiliary system (gall bladder, ampulla of vater, bile ducts); a gastric adenocarcinoma and a hepatoma were also above 37 units/ml. Additionally, 4 of 25 (16%) sera from lung cancer patients, 1 of 25 (4%) sera from breast cancer patients and 3 of 24 (12%) sera from other cancer patients (Table I) had elevated CA 19-9 levels. In two of these cases (357; 94 units/ml) the site of the primary tumor was unknown and in the third (39 units/ml) the site of the primary was the thyroid. Among 131 patients with benign diseases, only one (0.8%), a 47 year old male with interstitial pneumonitis of unknown etiology had elevated CA 19-9 (50.7 units/ml). As shown in Table 2, the benign disease group represented a broad range of gastrointestinal and non-gastrointestinal diseases, including 11 patients with benign pancreatic diseases, 52 patients with other gastrointestinaal diseases, and 68 with non-gastrointestinal diseases. Only 1 of 75 (1.3%) normal persons had elevated CA 19-9 (40.7 units/ml).

The mean CA 19-9 levels obtained for patient sera from all groups in the panel are presented in Table 3. The highest CA 19-9 levels were detected in sera of patients with pancreatic carcinoma (266 ±266 units/ml). CA 19-9 levels averaged 8.4±7.6 units/ml in normal individuals, 6.5±6.2 units/ml in patients with benign gastrointestinal disorders, 7.1±5.4 units/ml with benign pancreatic disease, and 8.6±9.5 units/ml with benign non-enteric disease. No statistically significant differences in these values could be found when patients were grouped according to age or fasting or nonfeeding, i.e. the CA 19-9 levels appeared to be independent of these parameters in the patient groups studied (data not shown).

Figure 3:
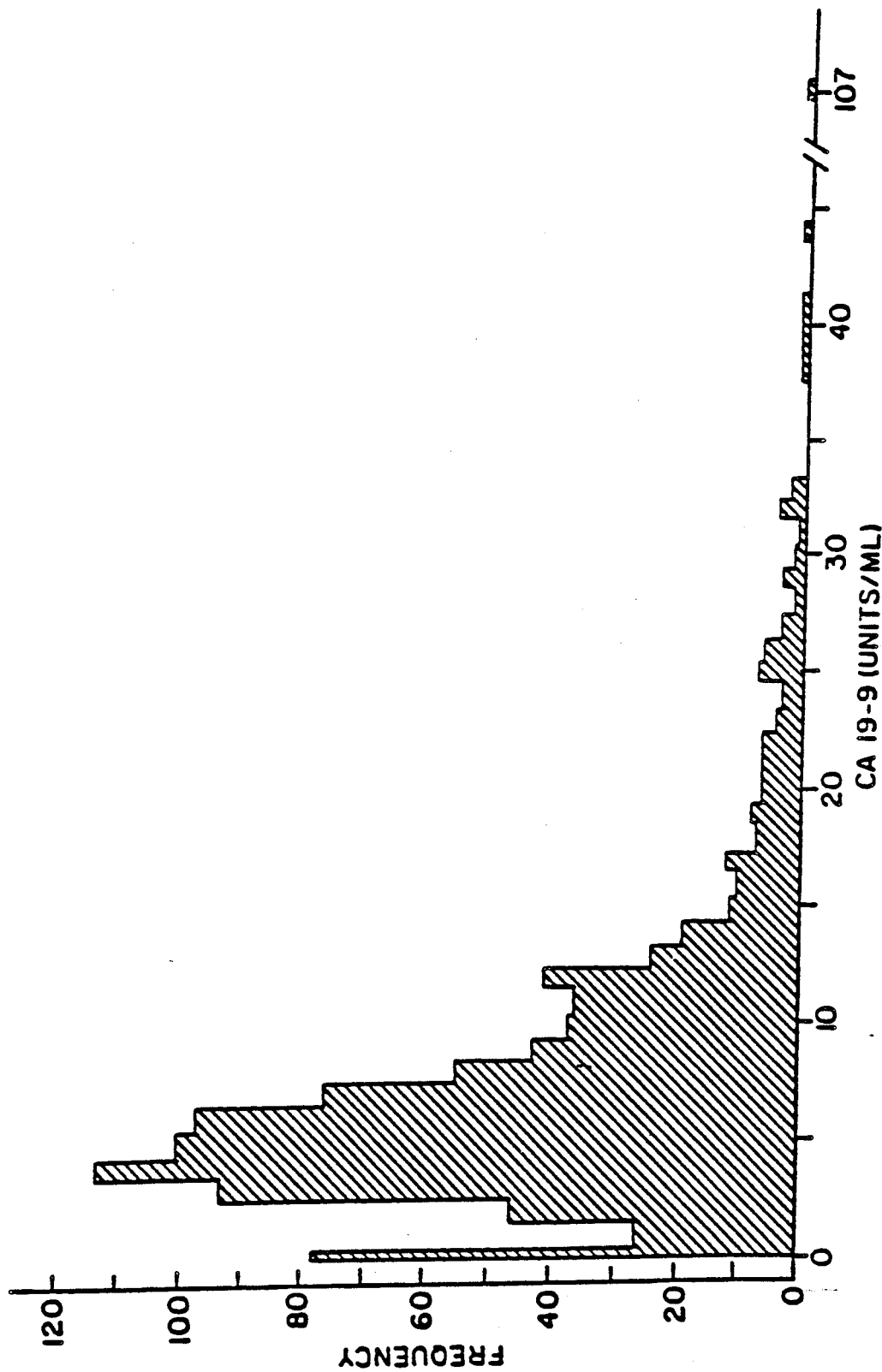
FIG. 3 is a plot illustrating the frequency of various CA 19-9 concentrations in sera from normal blood bank donors.

Sera obtained from randomly selected, healthy blood bank donors were evaluated using the CA 19-9 assay. As shown in FIG. 3, the mean for the normals was 8.7±7.4 units/ml (range 0–107 units/ml). Only 0.5% of these samples contained CA 19-9 at levels in excess of 37 units/ml. In addition, there was no statistically significant relationship between the age of the donors and the level of CA 19-9 in their sera. Small but statistically significant differences were observed between males and females. Females between 20 and 49 years of age had slightly higher levels than males. No further information could be obtained concerning the donors whose sera had elevated CA 19-9 levels.

The sensitivity of the CA 19-9 RIA for pancreatic cancer (74%) and the specificity among normal individuals (99.5%), and among patients with a wide variety of benign diseases (99.2%) were excellent. These benign diseases included benign pancreatic diseases, diabetes, arthritis and inflammatory gastrointestinal disorders.

CA 19-9 levels above 37 units/ml were observed in several patients with other gastrointestinal malignancies, particularly of the hepatobiliary system. Because the CA 19-9 antigen is present in normal tissues, especially the epithelial cells lining the ductules in the liver and pancreas, more extensive studies among patients with hepatobiliary tract disorders and pancreatitis will be required to assess reactivity in these patients.

CA 19-9 levels above 37 units/ml were observed in relatively few patients with colorectal cancer. Only 7% of patients with Dukes A, 16% of patients with Dukes B or C and 26% of patients with advanced metastatic colorectal disease had elevated CA 19-9 values.

Sera from some patients with non-gastrointestinal malignancies, especially lung tumors, had elevated levels of CA 19-9. In the four positive lung cancer patients, there was no apparent relationship to tumor type, grade or stage: Three were adenocarcinomas, grades 3 and 4, stages I, II, and III. The fourth was a squamous cell carcinoma, grade 3, stage I. Only one breast adenocarcinoma and one thyroid papillary carcinoma had elevated CA 19-9 levels.

To determine the effect of pH, a series of forward sandwich assays, as described above, were performed on samples prepared from one serum sample (PC 2). CA 19-9 antigen was purified from human ascites and then diluted into normal human serum. Samples were prepared by mixing serum-diluted CA 19-9 with either citrate or phosphate buffer and sufficient hydrochloric acid to produce the desired pH. The results are presented in Table 4.

TABLE 1

CA 19-9 Levels in Sera From Patients With Miscellaneous Cancer

| Diagnosis | CA 19-9 (units/ml) |
|---|---|
| Ampulla of Vater | 395.7 |
|  | 41.6 |
|  | 4.2 |
| Stomach | 535.6 |
|  | 7.9 |
|  | 0.0 |
| Hepatoma | 3:: 5 |
|  | 10.0 |
| Hepatic and Cystic Duct Cancer | 63.2 |
| Cancer Bile Duct | 151.5 |
|  | 112.8 |
|  | 23.3 |
| Gall Bladder | 640.8 |
|  | 528.2 |
|  | 5.0 |
| Appendix, Carcinoid | 0.0 |
| Ileum | 9.6 |
|  | 6.1 |
|  | 2.7 |
| Duodenum Cancer | 27.3 |
|  | 8.2 |
|  | 0.1 |
| Esophagus | 45.1 |
|  | 7.7 |
|  | 6.9 |
|  | 6.9 |
|  | 6.2 |
|  | 5.4 |
|  | 4.3 |
|  | 3.3 |
| Barrett's Esophagus | 5.4 |
| Primary unknown | 357.6 |
|  | 93.6 |
|  | 10.3 |
|  | 0.0 |
| Burkitt's Lymphoma | 17.9 |
| Lymphoma (Remission) | 20.8 |
| Leukemia | 8.6 |
|  | 7.1 |
| Hodgkin's Disease | 8.2 |
| Malignant Histiocytoma | 3.2 |
| Plasmacytoma (pulmonary) | 0.0 |
| Kidney | 16.5 |
|  | 5.9 |
| Bladder | 11.2 |
| Testicular | 9.0 |
| Prostate | 3.7 |
| Thyroid | 39.0 |
|  | 0.0 |
| Malignant Melanoma | 8.4 |
| Cancer Nasopharynx | 0.0 |
| Synovial Cell Sarcoma | 2.6 |
| Cancer Retroperitoneum | 3.3 |
| Osteogenic Sarcoma | 2.5 |
| Liposarcoma (thigh) | 1.2 |

TABLE 2

CA 19-9 Levels In Sera From Patients With Benign Diseases

| Diagnosis | CA 19-9 (units/ml) |
|---|---|
| Arthritis, Degenerative | 21.2 |
|  | 9.5 |
|  | 5.0 |
|  | 0.0 |
| Arthritis, Osteo | 15.1 |
|  | 5.3 |
| Arthritis, Rheumatoid | 5.7 |
|  | 3.9 |
|  | 0.2 |
| Arthritis | 5.4 |
|  | 4.7 |
|  | 4.4 |
| Degenerative Joint Disease | 16.0 |
|  | 9.1 |
|  | 4.4 |

TABLE 2-continued
CA 19-9 Levels In Sera From Patients With Benign Diseases

| Diagnosis | CA 19-9 (units/ml) |
|---|---|
|  | 1.9 |
| Hypothyroidism | 4.2 |
| Thyroiditis | 15.9 |
| Thyroiditis, Hashimoto's | 15.1 |
|  | 5.4 |
| Graves' Disease | 14.9 |
|  | 5.6 |
| Fibrocystic Disease (breast) | 13.7 |
|  | 5.0 |
| Gynecomastia | 5.4 |
|  | 4.2 |
| Psoriasis | 9.4 |
| Pancreatitis |  |
| Fatty Liver | 28.3 |
| Cirrhosis | 25.1 |
|  | 13.7 |
|  | 7.2 |
|  | 6.7 |
|  | 4.5 |
|  | 2.4 |
| Chronic Ulcerative Colitis | 15.7 |
|  | 3.8 |
|  | 3.6 |
|  | 1.5 |
|  | 0.0 |
|  | 0.0 |
| Diarrhea, unknown etiology | 14.6 |
|  | 13.2 |
| Irritable Colon/Bowel | 6.9 |
|  | 6.3 |
|  | 4.8 |
|  | 4.1 |
| Crohn's Disease | 6.8 |
|  | 0.0 |
| Achalasia | 5.0 |
|  | 0.2 |
| Post Vagotomy Diarrhea | 3.0 |
| Pyloric stenosis | 2.6 |
| Pneumonitis (interstitial, etiology unknown) | 50.7 |
| Systemic Mast Cell Disease (C.O.P.D.) | 35.3 |
| Pemphigus - vulgaris | 32.1 |
| Low Blood Pressure | 29.2 |
| Diabetes | 22.5 |
|  | 22.4 |
|  | 13.4 |
|  | 5.0 |
|  | 4.3 |
|  | 0.0 |
| Pericardial Cyst | 19.1 |
| Cholelithiasis | 14.5 |
| Hepatitis, Chronic, Acitive | 13.4 |
|  | 10.2 |
|  | 8.3 |
|  | 0.0 |
| Malabsorption Syndrome | 13.2 |
| Polyp | 12.3 |
| Ulcer(s) | 11.3 |
|  | 8.3 |
|  | 3.2 |
|  | 3.0 |
|  | 2.7 |
|  | 2.1 |
|  | 1.7 |
|  | 0.0 |
|  | 0.0 |
| Gastritis, Duodenitis | 10.3 |
|  | 8.9 |
|  | 6.3 |
|  | 5.0 |
|  | 2.0 |
| Intermediate Gastric Motility Disorder | 7.5 |
|  | 3.9 |
| Gastric Hypertension, Abdominal Pain | 7.3 |
| Granuloma | 11.0 |
|  | 10.2 |
|  | 4.4 |
|  | 4.3 |
|  | 2.9 |
| Benign Bone Cyst | 8.3 |
| Pregnancy | 6.8 |
| Thrombocytopenic purpura | 2.3 |
| Chronic alcoholism | 1.3 |
| Fibrosis | 4.4 |
| Turner's Variant | 0.0 |
| Dyspepsia | 0.0 |
| Unknown Abdominal Pain | 0.0 |
| Alcohol Abuse | 4.4 |
|  | 4.1 |
| Menometrorrhagia | 3.6 |
| Sarciodosis | 3.1 |
|  | 3.0 |
|  | 0.0 |
| Hyperplastic Mucosa | 3.5 |
| Polyps, cervical | 2.0 |
| Scoliosis | 2.7 |
| Hematoma | 4.9 |
| Thornwaldt's Disease | 4.1 |
| Aneurysm | 3.1 |
| Dumping Syndrome | 0.0 |
| Benign Prostatic Hypertrophy | 4.1 |
| Friction Blisters | 2.7 |
| Mixed Connective Tissue Disease | 1.8 |

TABLE 3
AVERAGE CA 19-9 CONCENTRATION IN PATIENT SERA

| | Group | n | Mean ± S.D. | Percent Positive[a] |
|---|---|---|---|---|
| A. | Cancers | | | |
| | Pancreas | 25 | 266 ± 266 | 74 |
| | Colon | | | |
| | Metastatic | 23 | 81.9 ± 168 | 26 |
| | Dukes B & C | 25 | 59.8 ± 123 | 16 |
| | Localized | 27 | 10.5 ± 14.2 | 7 |
| | GI (misc.) | 31 | 97.3 ± 182 | 32 |
| | lung | 25 | 52.8 ± 109 | 16 |
| | Breast | 25 | 10.3 ± 12 | 4 |
| | Other | 24 | 26.7 ± 73.1 | 12 |
| B. | Benign diseases | | | |
| | Pancreatic | 11 | 7.1 ± 5.4 | 0 |
| | Other GI | 52 | 6.5 ± 6.2 | 0 |
| | Non-GI | 68 | 8.6 ± 9.5 | 1.4 |
| C. | Normals | | | |
| | Normals | 75 | 8.4 ± 7.6 | 1.3 |

[a]Positive 37 units/ml

TABLE 4
Effect of Buffer pH on CA 19-9 Detected

| Buffer pH | CPM $^{125}$I-19-9 |
|---|---|
| 1.5 | 4680 |
| 2.0 | 5970 |
| 2.5 | 8880 |
| 3.0 | 9480 |
| 3.5 | 10860 |
| 4.0 | 23500 |
| 4.5 | 31100 |
| 5.0 | 26400 |
| 5.5 | 22800 |
| 6.0 | 14800 |
| 6.5 | 8260 |
| 7.0 | 4580 |
| 7.5 | 2870 |
| 8.0 | 2180 |

Industrial Applicability

The invention described herein is useful in the detection of carbohydrate antigenic determinants, such as CA 19-9. The assay can be employed by hospitals or clinical laboratories for the early detection of tumors, particularly pancreatic cancer tumors.

Equivalents

Those skilled in the art will recognize, or be able to ascertain, using no more than routine experimentation, many equivalents to the specific embodiments to the invention described herein Such equivalents are intended to be encompassed by the following claims.

We claim:

1. An immunoassay comprising:
   a) reacting an anti-CA19-9 antibody with a carbohydrate antigenic determinant CA19-9; and
   b) detecting the presence of a carbohydrate antigenic determinant CA19-9 in a sample;
   wherein the primary antigen-antibody reaction is carried out at a pH between about 2.5 and a pH of about 5.0.

2. An immunoassay of claim 1 wherein the pH is about 4.5.

3. An immunoassay of claim 1, wherein the detection of the carbohydrate antigen CA19-9 is indicative of human gastrointestinal adenocarcinoma.

4. An immunoassay of claim 1, wherein the detection of the carbohydrate antigenic determinant CA19-9 is indicative of pancreatic cancer.

* * * * *